United States Patent [19]
Bryker et al.

[11] Patent Number: 4,983,771
[45] Date of Patent: Jan. 8, 1991

[54] METHOD FOR RESOLUTION OF D,L-ALPHA-PHENETHYLAMINE WITH D(−)MANDELIC ACID

[75] Inventors: William Bryker, Hudsonville; Luis A. Avila, Holland, both of Mich.

[73] Assignee: Hexcel Corporation, Dublin, Calif.

[21] Appl. No.: 408,290

[22] Filed: Sep. 18, 1989

[51] Int. Cl.$^5$ .............................................. C07B 57/00
[52] U.S. Cl. ................................................. 564/304
[58] Field of Search .......................................... 564/304

[56] References Cited

FOREIGN PATENT DOCUMENTS 9110656  6/1984  Japan .
0104045  6/1985  Japan .

Primary Examiner—Paul J. Killos
Attorney, Agent, or Firm—Oblon, Spivak, McClelland, Maier & Neustadt

[57] ABSTRACT

A process for recovering optically pure D(+)alpha-phenethylamine which comprises addition of the racemic mixture to a water/acid solution, and as a resolving agent, optically active D(−)mandelic acid. An optically pure D(+)alpha-PEA mandelate salt is formed, crystallized out of solution and washed with water. The salt is broken with sodium hydroxide, or a similar base, and the D(+)PEA liberated is extracted with toluene. The D(+) PEA recovered by vacuum distillation is recovered in high yield, shows high enantiomeric purity.

9 Claims, No Drawings

METHOD FOR RESOLUTION OF D,L-ALPHA-PHENETHYLAMINE WITH D(−)MANDELIC ACID

BACKGROUND OF THE INVENTION

1. Field of the Invention:

The invention involves a method for the resolution of a racemic mixture of D,L-alpha-phenethylamine. Specifically, a method of resolving the racemic mixture with optically active mandelic acid provides for high yield recovery of D(+)phenethylamine with high enantiomeric purity.

2. Background of the Prior Art:

D(+)alpha-phenethylamine is a valuable intermediate in the manufacture of various pharmaceuticals. For instance, various anti-atherosclerosis agents may be prepared from fatty acid amides derived from this useful intermediate. See U.S. Pat. No. 3,980,698, Suzuki. However, given the impact of optical activity on bioavailability and pharmaceutical effectiveness, it is necessary to isolate the optical species from their racemates in high enantiomeric purity.

A wide variety of processes are known which use optically active acids in the resolution of this important intermediate. Thus, U.S. Pat. No. 2,276,508 is directed to the use of optically active tartaric acid. This patent requires several repeated and ordered crystallization steps, and does not provide for the recovery of the tartaric acid. In particular, this process requires enantiomeric purification of a solution, which may be quite difficult and expensive.

U.S. Pat. No. 4,129,580 describes the need to provide a resolving agent which can be used on a commercial scale, can be economically regenerated, and can be reused. Lasalocid (a polyether antibiotic) is identified as such an agent, but remains largely commercially unsatisfactory for the resolution of D,L-alpha-phenethylamine. One problem common to this and tartaric acid processes is the need to use large molar equivalents of the resolving agent.

U.S. Pat. No. 3,980,098 identifies a number of potential resolution agents for alkylphenyl ethylamines including optically active mandelic acid, but directs those of skill in the art away from such use due to the cost and lack of recovery of the resolving agent and difficulties encountered in purification. Column 1, lines 60–68.

In a similar process, D,L-phenylalanine is resolved with optically active mandelic acid in the presence of a stabilizing acid. U.S. Pat. No. 4,582,928. This patent uses the L-mandelic acid to recover the L-isomer desired, and does not provide for recovery of the resolving agent.

Accordingly, it remains an object of the art to provide a process for the resolution of D,L-alpha-phenethylamine that requires limited amounts of a recoverable resolving agents, while providing high yields and high enantiomeric purity.

SUMMARY OF THE INVENTION

The above objects, as well as others set forth below, are achieved by a process which resolves D,L-alpha-phenethylamine (PEA) by dissolving it together with D(-)mandelic acid in an aqueous solution comprising a second acid other than mandelic acid. Surprisingly, the (−)enantiomer of the resolving mandelic acid shows a marked preference for combination with the D(+)alpha-PEA. Thus, a diastereomic D(+)alpha-PEA D(-)mandelate salt is obtained. The second acid in solution combines with the remaining (−)-racemate, providing an aqueous soluble salt.

The mandelate salt is added to a NaOH/H$_2$O solution and pH is adjusted to a value of about 12.5–13.0. This cleaves the salt, releasing the D(+)alpha-PEA which may be extracted with toluene, the toluene being subsequently distilled off under vacuum, followed by the D(+)alpha-PEA. Overall yield is in the range of 75–80%, and enantiomeric purity is typically above 95%.

The remaining water solution used to cleave the mandelate salt may be treated for recovery of the D(−)mandelic acid resolving agent. Sufficient HCl or alternative acid is added to the water solution to neutralize the sodium mandelate. The resulting slurry is cooled to about 20°–25° C. The resolving agent may be extracted with methylisobutylketone (MIBK). The top MIBK extraction phases are combined and sufficient water is added to azeotrope off the MIBK and leave the mandelic acid in a 40–50% water solution. The D(−)mandelic acid water solution is cooled to about 40°–50° C. and recycled for further resolution. D(−)mandelic acid recovery is about 93–95% from the PEA/mandelate salt.

Additional mandelic acid can be recovered from the solution of the resolution mix. The L(−)alpha-PEA acid (e.g., acetate) salt is broken with NaOH. After adjustment to basic pH, the L(−)PEA is extracted with toluene at 20°–25° C. The toluene extraction(s) may be distilled under vacuum to recover, first, the toluene, and then the L(−)PEA.

The water phase remaining after toluene extraction of the L(−)PEA may be further treated to recover a minor portion of D(−)-mandelic acid. The water solution is acidified with a strong acid until a strongly acidic pH of about 1.0–1.5 has been reached. The D(−)mandelic acid may be removed with repeated extractions using MIBK. The extractions are combined with an amount of water sufficient to azeotrope off and leave the D(−)-mandelic acid as a 40–50% solution. Both quantities of the MIBK may be recycled for further extractions. The mandelic acid water solution is cooled to 40°–50° C. and can be used for further resolution. The two recoveries of D(−)mandelic acid results in an overall return of 85–95%.

DETAILED DESCRIPTION OF THE INVENTION

The invention begins with preparation of the racemic mixture of D,L-alpha-phenethylamine. The racemic mixture is the natural product of most preparations, and is well documented in the art.

The racemic mixture is added to a water/acid solution, to which is also added D(−)mandelic acid. The acid in the water solution can be virtually any acid capable of forming a water-soluble salt with the L(−)PEA released by the resolution reaction. Among exemplary acids are acetic acid, sulfuric acid, and similar commonly available acids. Related organic acids, such as propionic and butyric acid may also be used. A preferred acid is acetic acid. To the water/acids/D(−)-mandelic acid mixture is added the racemic PEA preparation. This addition results in an exothermic reaction, and should accordingly be done over a limited time period. About 10–30 minutes is adequate. Generally, the reaction mixture results in a clear solution, but the mixture can be mildly heated, under the boiling point of the mixture, until a clear water solution is obtained. After this clear solution is obtained, the solution is slowly cooled, to about 50° C.

This invention is premised on the surprising discovery that D(−)mandelic acid shows a marked preference for combination with the D(+)alpha-phenethylamine stereoisomer, to such an extent that the reaction proceeds to essential completion even in the absence of an equivalent amount of PEA, prior to resolution, and resolving agent. Thus, about 0.4–0.6, preferably about 0.5 to 0.55 moles of D(−)mandelic acid is used for each mole of racemic PEA added. To form the L(−)PEA acetate, 0.9 to 0.6, preferably 0.45 to 0.55 moles of acetic acid are used. During the cooling of the solution, the D(+)PEA-mandelate salt crystallizes out of solution. The resulting slurry is cooled to about 10°-20° C., and held for a period of hours. No cooling rate or holding period is critical, but a preferred cooling period of about 1-3 hours may be advantageously employed.

The resulting crystallized material is filtered through conventional physical filtering processes, and washed with cold water to displace remaining L(−)PEA acetate (or similar acid) salt after filtering. In order to secure an enantiomerically pure resolution, this washing is a critical step.

The D(+)PEA-D(−)mandelate salt may be dried, purely for purposes of yield and quality determination. Typically, the yield of the isolated salt runs from 80-90%. The enantiomeric purity of the salt is greater than 95% and typically 98-99%.

The optically pure salt is treated with an aqueous sodium hydroxide or equivalent base solution. Equivalent amounts of NaOH or other base (based on the mandelate salt) is added to water. In general, the amount of water necessary is at least 1.6 times the dry weight of the salt, although excess water may be employed. While the resulting sodium hydroxide/water solution is stirred, the dry D(+)PEA/mandelate salt is added. If not already there, the pH is adjusted with additional NaOH to bring the pH of the water solution to approximately 12.5-13.0, cleaving the salt and releasing the D(+)PEA.

The desired stereoisomer is extracted from the D(−)Na-mandelate water solution with toluene at 30°-35° C. For reasons unknown, the D(+)PEA-D(−)Na-mandelate water mixture does not neatly divide into two separate phases, and accordingly, a plurality of toluene extractions is frequently necessary. Very careful extraction processing may reduce the number of extractions necessary, at the sacrifice of certain commercial efficiencies. The resulting toluene/D(+)PEA extractions are combined and loaded to a vacuum distillation unit. The first fraction recovered is the toluene, distilled forward generally under about 20-22 inches, followed by D(+)alpha-PEA under about 27-29 inches. A high yield of D(+)PEA is recovered from the mandelate salt, generally about 95% or better. Overall this represents a yield of about 75-85%. The specific optical rotation of the distilled D(+)PEA ranges from 36.3 to +39.7.

As noted, an important feature of this invention is that it provides for straightforward recovery of the resolving agent, D(−)mandelic acid. As disclosed above, the mandelic acid is in the form, after breaking of the optically pure PEA/mandelate salt, in the form of a D(−)Na-mandelate water solution. This solution is fed to an equivalent amount of strong acid, e.g., 30-32% HCl. Other acids, capable of neutralizing the solution can be used, and the identity of the acid is not critical. Alternative acids include sulfuric acid, nitric acid, phosphoric acid, and various organic acids, such as acetic acid. The amount of acid added is based on the amount of 50% NaOH loaded in the previous procedure. The resulting D(−)-mandelic acid/water slurry is cooled, to about 20°-25° C. The D(−)-mandelic acid can be extracted from the water slurry with MIBK. Again, generally, repeated extractions are necessary to completely extract the acid.

To the combined extractions is added sufficient water to distill the MIBK/water azeotrope forward and leave the D(−)-mandelic acid behind as a 40-50% water solution. Typically, about 95% of the MIBK is recovered. The D(−)mandelic acid water solution is cooled to 40°-50° C., and recycled for further resolution reactions. The yield from the mandelic acid/D(+)PEA salt is about 93-94%.

Further optically active mandelic acid can be recovered from the filtrate of the resolution reaction, accompanied by the isolation of L(−)PEA. Some of this additional D(−)mandelic acid is present in the unpreferred salt form. The filtrate is comprised mostly of the L(−)PEA/acid (e.g., acetate) salt. This salt is not optically pure, as directly recovered, and is racemized to D,L-alpha-PEA, which is recycled back into the resolution reaction or purified to enantiomerically pure L(−)PEA.

The L(−)PEA acetate salt is broken with 50% sodium hydroxide. After adjustment of the pH to about 12.5-13.0 with NaOH, the resulting solution is straightforwardly extracted with toluene at about 20°-25° C. If repeated extractions are necessary, they are combined, and distilled under partial vacuum to recover the toluene and L(−)PEA, in a fashion similar to that employed to recover the enantiomerically pure D(+)PEA, described above. The remaining water phase is acidified with an equivalent amount of acid, as described above, in conjunction with mandelic acid recovery, based on the amount of sodium hydroxide previously loaded. After an acid pH of about 1.0-1.5 is achieved, extraction of mandelic acid with MIBK, as practiced previously, is used to extract the mandelic acid. Again, repeated extractions may be necessary to totally recover all D(−)mandelic acid. The extractions are combined with a sufficient amount of water to distill the MIBK forward, as the MIBK/water azeotrope and leave the D(−)mandelic acid behind, as a 40-50% water solution. The optically active mandelic acid/water solution is again cooled to 40°-50° C., and held for further resolution, as described above. A typical return of about 70-80% of D(−)mandelic acid from the salts in the filtrate is achieved. As noted, the overall return of D(−)mandelic acid is between 85-90%.

EXAMPLE I

A. Resolution Reaction

To a solution of 327.5 grams of $H_2O$, 120.0 grams acetic acid and 334.7 grams D(−)mandelic acid, said solution having been stirred at raw temperature, was added 484.0 grams D,L(+)alpha-phenethylamine (PEA). The temperature of the solution rose from 18° C. to 63° C., and was further heated to 75° C. The bath was subsequently cooled to 15° C. and held at that temperature for 5 hours. Precipitation of crystalline material began at about 63° C. After further cooling to 15° C., the precipitate was filtered and washed with 130 grams of tap water. The dry weight of the (+)PEA(−)mandelate salt (469.0 grams) represents an 85.8% yield.

B. Recovery of D(+)PEA 469.0 grams (dry weight) of the (+)PEA mandelate salt was added to a solution of 760 grams tap water and 137.3 grams of a 50% NaOH solution. The resulting mix was extracted 4 times with toluene, for a total of 775 grams of toluene added. The toluene phase was separated and subjected to vacuum distillation, recovering 757 grams of toluene (97.7% return) and 194.4 grams of D(+)PEA. The enantiomerically pure composition gave an optical rotation of 37.5 degrees. The theoretical PEA recovery from this salt was 93.8%.

C. Recovery of Mandelic Acid.

The sodium mandelate solution not treated above was neutralized with 209 grams HCl for a pH of 1-2.0. It was extracted 4 times with MIBK, for a total addition of MIBK of 525 grams. To this was added 510 grams $H_2O$, and the MIBK was distilled by azeotropic distillation. 498.5 grams of MIBK was recovered, giving a 95% recovery. A 42% mandelic acid in water solution was recovered, 582.7 grams, or 246.54 grams of mandelic acid.

D. Isolation of L(−)PEA and Recovery of Mandelic Acid

To the filtrate remaining after process A above was added 201 grams of 50% sodium hydroxide solution, for a pH of 12.9. The basic solution was extracted 3 times with toluene, for a total toluene addition of 325 grams. The toluene and (−)PEA were distilled off under vacuum, resulting in a recovery of 303.6 grams (93.4%) of toluene, and L(−)PEA in about 260.2 grams. The sodium mandelate/sodium acetate phase was neutralized with 305.4 grams HCl, giving a pH of about 0.8. This was extracted 4 times with MIBK, in a fashion similar to that above, for a total addition of 295.3 grams MIBK. 185 grams $H_2O$ was added to the MIBK, and the MIBK was distilled off with azeotropic distillation, returning 274.4 grams or 92.9% MIBK recovery. The mandelic acid recovered from this process, together with that recovered above, gave a total recovery of 299.44 grams mandelic acid, or an 89.5% return.

Thus, as described, a process is provided which yields, in essentially one step, an enantiomerically pure PEA salt, which may be easily recovered with toluene extraction. Not only is this process simple and straightforward, but it provides for the recovery of the resolving agent, mandelic acid, in extremely high amounts, generally about 90%. This provides significant commercial advantages, overcoming teachings in the art, discussed above, against the use of optically active mandelic acid. As noted, one critical element which makes this possible is the marked preference for D(−)mandelic acid for combination with the "optical opposite" PEA, that is, D(+)alpha-PEA. By recovering mandelic acid from both the PEA/mandelate salt, and the resolution filtrate, significant commercial advantages are achieved.

The above invention has been described both in terms of general description, and with specific embodiment. The embodiments are not intended to be limiting, except where so indicated and alternatives will occur to those of ordinary skill in the art without the exercise of inventive faculty. In particular, substitute acids, amounts, and temperature ranges may be safely used, without departing from the spirit of the invention, as defined in the claims attached hereto.

What is claimed is:

1. In a process for the optical resolution of a racemic mixture of D, L(−+)-α-phenethylamine (PEA), wherein said PEA is added to a solution of a solvent and D(−)mandelic acid to form a D(+)α-PEA-mandelate salt, which is recovered from said solution broken with a base and extracted with an organic solvent, the improvement comprising:

using, as said solvent, a water/acid solution, said water/acid solution containing sufficient acid to combine with substantially all L(−)PEA introduced to said solution, and wherein the amount of mandelic acid employed as a resolving agent is the molar equivalent of substantially all D(+)α-PEA added to said solution.

2. The process of claim 1, further comprising recovering D(−)-mandelic acid from said water/base solution after said extraction step E, by the sequential steps of:

G, neutralizing said water/base solution by addition of acid thereto,

H, cooling the resulting slurry,

I, extracting D(−)mandelic acid from said slurry with methylisobutylketone (MIBK), and J, adding sufficient water to all said MIBK extraction to azeotrope off the MIBK and leave the D(−)mandelic acid as a 40-50% water solution.

3. The process of claim 1, further comprising recovering D(−)mandelic acid from the filtrate solution after recovery of said salt, by the sequential steps of:

L, breaking any L(−)PEA containing salt in said filtrate by addition of base to said solution, and adjusting the pH of the resulting solution to about 12.5-13.0, M, extracting the pH adjusted solution of step L with toluene to remove L(−)PEA and vacuum distilling the resulting extract to recover toluene and L(−)PEA, N, adding a strong acid to the solution remaining after the extraction of step M until a pH of about 1.0-1.5 is reached, O extracting D(−) mandelic acid in said solution with MIBK, and P, adding sufficient water to azeotrope off said MIBK, leaving the remaining D(−)mandelic acid as 40-50% water solution.

4. The process of claim 2, further comprising recovering D(−)mandelic acid from the filtrate solution remaining after recovery of said salt, by the sequential steps of:

L, breaking any L(−)PEA containing salt in said filtrate by addition of base to said solution, and adjusting the pH of the resulting solution to about 12.5-13.0, M, extracting the pH adjusted solution of step L with toluene to remove L(−)PEA and vacuum distilling the resulting extract to recover toluene and L(−)PEA, N, adding a strong acid to the solution remaining after the extraction of step M until a pH of about 1.0-1.5 is reached, O extracting D(−) mandelic acid in said solution with MIBK, and P, adding sufficient water to azeotrope off said MIBK, leaving the remaining D(−)mandelic acid as 40-50$ water solution.

5. The process of claim 1, wherein said base is sodium hydroxide.

6. The method of claim 1, wherein the acid of said water/acid solution is selected from the group consisting of acetic acid, sulfuric acid, propionic acid, butyric acid and mixtures thereof.

7. The process of claim 3, wherein the base added in step L is sodium hydroxide, and the acid added in step N is selected from the group consisting of hydrochloric acid, sulfuric acid, nitric acid, phosphoric acid, low molecular weight organic acids and mixtures thereof.

8. The process of claim 4, wherein 85-95% of the mandelic acid present in the solution is recovered.

9. The process of claim 1, wherein the D(+)alpha-PEA recovered has a enantiomeric purity of greater than 95%.

* * * * *